United States Patent [19]
Delannoy et al.

[11] Patent Number: 4,966,657
[45] Date of Patent: Oct. 30, 1990

[54] PROCESS FOR SEPARATING ETHYLENE OXIDE FROM ALDEHYDE IMPURITIES BY DISTILLATION

[76] Inventors: Francis Delannoy, 61, Rue Ampere, 69310 Pierre-Benite; Gerard Letray, Rue Docteur Postel, 76620 Le Harve, both of France

[21] Appl. No.: 285,216

[22] Filed: Dec. 16, 1988

[30] Foreign Application Priority Data

Dec. 22, 1987 [FR] France ................................ 87 18246

[51] Int. Cl.⁵ ...................... B01D 3/38; C07D 301/32
[52] U.S. Cl. ........................................ 203/76; 203/77; 203/87; 203/92; 203/93; 549/541
[58] Field of Search ....................... 203/91, 92, 42, 76, 203/77, 93, 83, 87, 96; 549/541, 538

[56] References Cited

U.S. PATENT DOCUMENTS

| | | | |
|---|---|---|---|
| 2,615,901 | 10/1952 | McClellan | 549/541 |
| 3,165,539 | 1/1965 | Lutz | 549/541 |
| 3,265,593 | 8/1966 | Leis et al. | 203/60 |
| 3,418,338 | 12/1968 | Gilman et al. | 203/75 X |
| 3,745,092 | 7/1973 | Vanderwater | 549/541 |
| 4,134,797 | 1/1979 | Ozero | 203/75 |
| 4,778,567 | 10/1988 | Kakimoto et al. | 549/541 |

FOREIGN PATENT DOCUMENTS 139601 5/1985 European Pat. Off. ............ 549/541

OTHER PUBLICATIONS

French Search Report FR 8718246 dated Aug. 23, 1988.

*Primary Examiner*—Wilbur Bascomb
*Attorney, Agent, or Firm*—Sigalos, Levine & Montgomery

[57] ABSTRACT

An improved process for separating ethylene-oxide from formaldehyde and acetaldehyde in contaminated ethylene oxide, the process involves introducing the contaminated ethylene oxide into a reflux column and distilling the contaminated ethylene oxide under conditions such that the fluid stream leaving the bottom of the reflux column contains the water present in the contaminated ethylene oxide and the ethylene oxide in amounts corresponding, on a weight basis, to 0.15 to 3 times the weight of the water, and the ethylene oxide resulting from the separation of the formaldehyde and acetaldehyde leaves the column at its top.

13 Claims, 1 Drawing Sheet

PROCESS FOR SEPARATING ETHYLENE OXIDE FROM ALDEHYDE IMPURITIES BY DISTILLATION

BACKGROUND OF THE INVENTION

The present invention pertains to a process for separating ethylene oxide from aldehyde-type impurities; formaldehyde as well as acetaldehyde.

Ethylene oxide accompanied by the said impurities essentially results or derives from the production of ethylene oxide by gas-phase catalytic oxidation of ethylene by molecular oxygen.

The ethylene oxide is isolated from the gaseous mixture formed in the zone of catalytic oxidation of ethylene in a known manner, usually in several steps comprising:

(a) absorption by water, consisting of bringing the said gaseous mixture into contact with water to obtain an aqueous solution of ethylene oxide usually containing about 2–3 wt.% ethylene oxide, aldehyde-type impurities and, in the dissolved state, normally gaseous compounds, especially $CO_2$, (b) desorption, consisting of subjecting the dilute ethylene oxide solution obtained in (a) to steam distillation to obtain a gaseous mixture containing $CO_2$ and aldehyde-type impurities, formaldehyde and acetaldehyde, in addition to ethylene oxide, which is usually present in amounts of 30–60 wt.%, (c) reabsorption by water of the ethylene oxide contained in the gaseous mixture obtained in (b) to form an 25 aqueous ethylene oxide solution usually containing about 5–25 wt.% ethylene oxide and also $CO_2$, as well as aldehyde-type impurities, and (d) distillation of the aqueous ethylene oxide solution obtained in (c) to obtain ethylene oxide with little or practically no water, on the one hand, and an aqueous stream practically free from ethylene oxide, on the other hand.

The ethylene oxide thus obtained in (d) contains a level of aldehyde-type impurities, formaldehyde and acetaldehyde, that is so high that it is not possible to reach the quality required industrially.

U.S. Pat. No. 4,134,797 proposes a process for reducing the aldehyde-type impurity content in ethylene oxide, according to which an aqueous stream essentially free from ethylene oxide is drawn off at the bottom of the column used. This depletion of ethylene oxide in the said aqueous stream is guaranteed by the introduction of steam as a distilling fluid into the column. The ethylene oxide leaves the column simultaneously at three different levels in the form of a stream of ethylene oxide rich in formaldehyde, a stream rich in acetaldehyde and finally a stream of ethylene oxide that may contain about 0.001–0.035% aldehyde-type impurities. This latter stream is obtained only as a result of a very complex distillation process which leaves about 25–40% of the ethylene oxide in the nonpurified form according to the examples described.

SUMMARY OF THE INVENTION

The process according to the present invention is suitable for separating ethylene oxide from formaldehyde and acetaldehyde in an ethylene oxide stream that may contain, in addition to these impurities, any amount of water. This process can be carried out so as to ensure recovery of almost the total amount of the ethylene oxide in the purified form. It only requires a simple and single distillation step. It is suitable for separating formaldehyde as well as acetaldehyde. It is mainly of interest for the separation of both formaldehyde and acetaldehyde.

Briefly stated, the present invention comprises an improved process for separating ethylene-oxide from formaldehyde and acetaldehyde in contaminated ethylene oxide comprising introducing the contaminated ethylene oxide into a reflux column and distilling said contaminated ethylene oxide under conditions such that the fluid stream leaving the bottom of said reflux column contains the water present in the contaminated ethylene oxide and the ethylene oxide in amounts corresponding, on a weight basis, to 0.15 to 3 times the weight of the water, and the ethylene oxide resulting from the separation of the formaldehyde and acetaldehyde leaves said column at its top.

DETAILED DESCRIPTION

Figure 1:
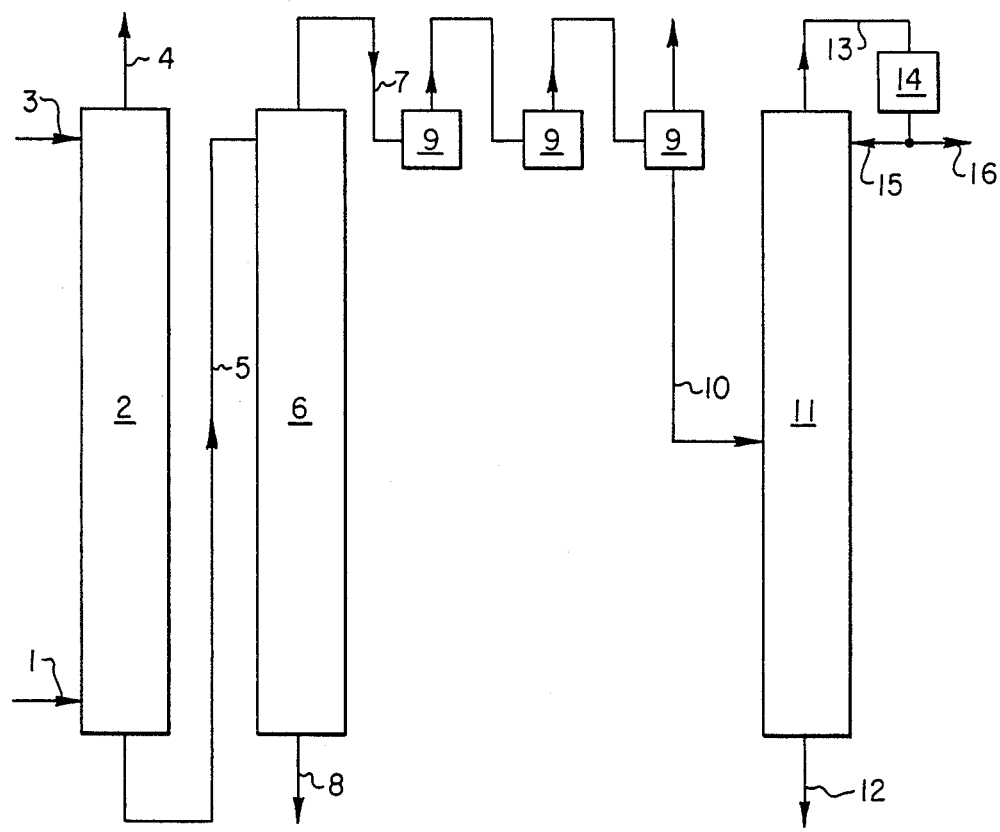
FIG. 1 is a schematic representation of an apparatus system for carrying out the process of the present invention.

This process leads to ethylene oxide separated from formaldehyde and, simultaneously, acetaldehyde, e.g., from:

(i) a stream of contaminated ethylene oxide resulting from a step such as (d) according to the prior-art process noted above or the streams of contaminated ethylene oxide as mentioned in the above-mentioned U.S. Pat. No. 4,134,797 (water is added to these streams if necessary); or (ii) a stream of ethylene oxide resulting from a step such as (b) noted above, particularly the liquid stream leaving the last heat exchanger during the progressive condensation of a gas stream discharged at the top of the desorption column in a step (b) when the said condensation is carried out in two or three heat exchangers arranged in series analogously to that described, e.g., in European Patent Application No. EP-0,139,601. A process for producing ethylene oxide, in which the process of isolating ethylene oxide from the gas stream discharged from the catalytic oxidation zone comprises an isolation according to (a), a desorption according to (b) with progressive condensation of the top gas stream as defined above and separation of the ethylene oxide from formaldehyde and acetaldehyde according to the present invention, is thus particularly attractive because of its simplicity and economy.

Even though the process according to the present invention is applicable to the intended separation from ethylene oxide containing up to about 75 wt.% water, it is most valuable in practice when the proportion of water is equal to or lower than about 20 wt.% and even 10 wt.% considering the ease with which the water content can be brought to the latter values. The amount of water in the contaminated ethylene oxide is preferably not lower than about 0.5 wt.% so that the column can function with ease.

It is also normally advantageous in correspondence with the intended separation that a liquid stream leaving the column at its bottom only contains a limited percentage of ethylene oxide present in the contaminated product as is easily made possible by the invention. The amount of ethylene oxide (on a weight basis) in the said stream is most often between 0.3 and 1.5 times the amount of water.

The amount (on a weight basis) of aldehyde-type impurities, formaldehyde and acetaldehyde, in the contaminated ethylene oxide relative to that present in the ethylene oxide can vary within rather broad limits, e.g., those specified in U.S. Pat. No. 4,134,797. In practice, the contaminated ethylene oxide most often contains about 0.005 to 0.2 wt.% of the said aldehydes relative to the weight of the ethylene oxide present; the ratio of formaldehyde to acetaldehyde is not critical for the present invention.

In the particular case in which the method just described is applied to the separation of ethylene oxide from aldehyde-type impurities in an ethylene oxide of the type that results from the above-mentioned progressive condensation in the citation of European Patent Application No. EP-0,139,601, the said contaminated ethylene oxide may contain at least about 95 wt.% and often more than 97 wt.% ethylene oxide and generally about 0.005–0.05 wt.% aldehyde-type impurities.

If compounds that are normally in the gaseous state, such as essentially $CO_2$, are present in the dissolved state in the contaminated ethylene oxide, they are preferably practically expelled in a known manner prior to distillation, e.g., by degassing or stripping by simple heating under pressure of the contaminated ethylene oxide.

The separation of ethylene oxide from aldehyde-type impurities in the process according to the present invention is carried out in a conventional distilling column, e.g., in a plate-type column in which the theoretical number of plates is, e.g., about 50, but it may often be between ca. 30 and 60 depending on the particular case, the said column operating under an absolute mean pressure that is most often between about 2.5 and 5 bars, so that under the preferred operating conditions, the desired weight ratio of the ethylene oxide to the water determined at the bottom of the column can be maintained at a temperature tat is most often between about 40° C. and 60° C. in this zone. The contaminated ethylene oxide is charged into the column at a level that is preferably located between approximately half and three-fourths the theoretical number of plates counted from the top. The thermal energy needed is supplied for the column, for example, by reboiling at the bottom with reboilers fed with steam or an adequate stream in an ethylene oxide production unit, such as the gaseous stream discharged at the top of the desorption column mentioned above under (b). The ethylene oxide resulting from the separation of the aldehyde-type impurities leaves the column at the top in the form of a gas stream that is subsequently condensed. Part of the condensate returns into the column as a reflux at the top of the column, whereas the complementary nonrefluxed part constitutes the ethylene oxide product stream.

The ratio of the refluxed ethylene oxide to the ethylene oxide produced may vary within relatively broad limits. In general, it is between 1:1 and 9:1, most often between 1.5:1 and 6:1.

The said ethylene oxide produced only contains an amount of aldehyde-type impurities, formaldehyde and acetaldehyde, that is usually lower than about 0.0025 wt.% and often ca 0.0015 wt.%, in addition to an amount of water that does not usually exceed 0.002 wt.%.

The formation of transformation products of ethylene oxide, such as glycols, is practically negligible in the process according to the present invention. The liquid stream leaving the bottom of the distillation column in the process according to the present invention can be treated, e.g., to transform the ethylene oxide into glycol in a known manner and then to separate the aldehyde-type impurities from the glycol to remove them from the production circuit.

FIG. 1, the single sheet of drawings, schematically illustrates the extremely simple process of isolating ethylene oxide that is made possible by the process according to the present invention in a process of producing ethylene oxide by gas-phase catalytic oxidation of ethylene by oxygen.

In the scheme, an absorption column of step (a) and a desorption column of step (b) operating under known conditions are designated by 2 and 6, respectively, while the column, in which the ethylene oxide is separated from its aldehyde-type impurities which is adapted to the realization of the present invention, is designated by 11.

The gas stream 1 coming from the ethylene catalytic oxidation zone enters the lower level of the absorption column 2 that operates under pressure and comprises a multiplicity of theoretical stages or gas-liquid contact devices to be brought into counterflow contact with the absorbent stream 3 mainly formed by water and entering the column 2 at a higher level. The gas stream 4, which leaves at the top of 2, contains trace amounts of ethylene oxide, ethylene, oxygen, $CO_2$ and inert gases. After its $CO_2$ content is reduced, this gas stream is recycled in a known manner in the ethylene oxidation step. The liquid aqueous stream 5 leaving the column 2 at its bottom contains ethylene oxide at a concentration that is often only slightly different from 2–3 wt.%, dissolved gases, especially $CO_2$, and aldehyde-type impurities.

The stream 5 enters column 6 at an upper level so that the ethylene oxide it contains is extracted with steam in the form of the gas stream 7 that most often contains ca. 30–60 wt.% ethylene oxide, water and aldehyde-type impurities. This stream may not practically contain any dissolved gas if the stream 5 is treated, e.g., according to the process described in European Patent Application No. EP-0,149,585. However, it contains aldehyde-type impurities. The aqueous stream 8 leaving the column 6 at its bottom is cooled and is essentially used as the absorbent stream 3.

The stream 7 is progressively condensed in two or three heat exchangers 9.

In terms of structure and function, the column 6 and the heat exchangers 9 are the same as those described in European Patent Application No. EP-0-139,601.

The liquid stream 10 leaving the last heat exchanger and from which the gases still present can be removed, if necessary, in a known manner, e.g., by degassing, as was mentioned above, contains, as was indicated above, generally more than ca. 95 wt.%, often at least 97 wt.%, ethylene oxide, and up to 0.2 wt.%, most often between 0.005 wt.% and 0.05 wt.%, aldehyde-type impurities, in addition to water.

It enters the distillation column 11 that ensures the separation of ethylene oxide from aldehyde-type impurities in that structure and in the operation already described.

The liquid stream leaving the column 11 at its bottom is designated by 12. It contains ethylene oxide and water in a weight ratio corresponding to the definition given in the present invention.

The gas stream leaving column 11 at the top, which consists of ethylene oxide resulting from the separation according to the present invention, is designated by 13. It is condensed in 14 to make it part of the liquid reflux 15 introduced into the column 11 at its higher level and of the stream 16 of the ethylene oxide product.

The present invention will be further described and compared to the state of the art by the examples given below which are set forth for purposes of illustration only. In the examples, the weight data higher than 100 kg are rounded to the nearest kg and FIG. 1 of the single sheet of drawings is used as a reference.

EXAMPLE 1

In a process for producing ethylene oxide by the gas-phase catalytic oxidation of ethylene by oxygen, which comprises a process for isolating the ethylene oxide according to the simplified scheme shown in FIG. 1, the dilute aqueous solution of ethylene oxide obtained at the bottom of the absorption column 2 is freed from most of the gases dissolved in it by applying the technique described in European Patent Application No. EP-0,149,585 (not shown).

The solution is subsequently subjected in column 6 to desorption of the ethylene oxide with progressive condensation of the resulting as stream in three heat exchangers 9 according to the technique described in European Patent Application No. EP-0,139,601.

The gas stream leaving the column 6 at its top contains aldehyde-type impurities and essentially consists of ethylene oxide and water.

Even though it may not be necessary, the liquid stream leaving the last of the three heat exchangers is freed from the gases which might still be dissolved in it by evacuating them by heating in a column (not shown) according to well-known technology. The liquid stream entering at the upper level of this degassing column leaves this column at the bottom at a temperature and under an absolute pressure equal 63° C. and 5.6 bars, respectively, in this case. This forms the contaminated ethylene oxide obtained at a rate of 5,755 kg/hour and containing 97.4 wt.% ethylene oxide and 2.6 wt.% water; these values were not corrected for the 0.011 wt.% aldehyde-type impurities consisting of 0.0085 wt.% acetaldehyde and 0.0025 wt.% formaldehyde, nor for the other products present in trace amounts.

This enters the column 11, which contains 50 theoretical plates, at the level of the 30th plate counted from the top.

Column 11, which operates under a mean absolute pressure of 2.7 bars, is supplied with heat in the conventional manner by indirect heat exchange between the steam and the liquid at the bottom, whose reboiling is thus ensured. The temperature of the liquid at the bottom of the column equals 42° C. The flow rate of the liquid stream leaving the column at its bottom is 290 kg/hour. This stream contains 51.5 wt.% water and 48.3 wt.% ethylene oxide and is sent to a glycol production unit.

A gas stream consisting of ethylene oxide and only containing about 0.0015–0.0020 wt.% aldehyde-type impurities, including no more than about 0.0005 wt.% formaldehyde, leaves the top of column 11 at a temperature of 35.4° C. The traces of water present in this stream are not taken into account here.

A fraction of the liquid obtained by condensing the said gas stream is returned into column 11 as a reflux at a higher level, while the complementary fraction, obtained at a rate of 5,465 kg/hour, forms the ethylene oxide product, the weight ratio of ethylene oxide refluxed to ethylene oxide product being 1.5:1.

EXAMPLE 2

(COMPARATIVE)

In a process for isolating the ethylene oxide from the gas stream leaving the zone of vapor-phase catalytic oxidation with oxygen, which comprises steps (a), (b), (c) and (d) of the prior-art technique as defined at the beginning of the text, the stream of ethylene oxide obtained in (d) contains 0.01% aldehyde-type impurities, in addition to traces of water.

This stream, which is obtained at a flow rate of 5,700 kg/hour, is distilled off in column 11 according to Example 1, in which the same conditions in terms of absolute mean pressure and reflux are used. A liquid stream essentially consisting of ethylene oxide is obtained at the bottom of this column at a temperature equaling 40° C. and at a flow rate of 143 kg/hour, such that the amount of ethylene oxide thus evacuated hourly at the bottom of the column is almost the same as in Example 1.

The ethylene oxide product stream is obtained at a flow rate of 5,557 kg per hour. It consists of ethylene oxide, that is, of course, practically anhydrous, but still contains aldehyde-type impurities in an amount equaling 0.0045 wt.%, i.e., about 2.5 to 3 times as much as the ethylene oxide produced in Example 1. Practically all the formaldehyde initially present in the contaminated ethylene oxide is present in the ethylene oxide produced.

EXAMPLE 3

Example 1 is repeated by evacuating a liquid stream containing 59.9 wt.% ethylene oxide and 39.9 wt.% water at a rate of 374 kg/hour at the bottom of column 11 at a temperature equaling 40° C.

The ethylene oxide produced at a rate of 5,381 kg/hour contains an amount of aldehyde-type impurities that is below 0.0015%, which always contain less than 0.0005% formaldehyde.

EXAMPLE 4

Operating as in Example 1 but withdrawing a liquid stream containing 40 wt.% ethylene oxide and 59.8 wt.% water at a rate of 250 kg/hour at the bottom of column 11 at a temperature equaling 44° C., the ethylene oxide produced at a rate of 5,505 kg/hour contains, on an average, only 0.0022 wt.% aldehyde-type impurities, which contain at most 0.0005 wt.% formaldehyde.

EXAMPLE 5

Contaminated ethylene oxide containing 94.8 wt.% ethylene oxide, 5.2 wt.% water and 0.011 wt.% aldehyde-type impurities (formaldehyde and acetaldehyde) is distilled in column 11 at a flow rate of 5,755 kg/hour as in Example 1, with the difference that the stream is now withdrawn at the bottom of this column at a flow rate of 600 kg/hour and this stream contains 50 wt.% water and 50 wt.% ethylene oxide.

The ethylene oxide produced again contains less than 0.0015 wt.% aldehyde-type impurities, one-third of which is formaldehyde.

Under the same conditions as above, the distillation of a contaminated ethylene oxide containing 0.011% aldehyde-type impurities, but only about 0.001% formaldehyde, leads to the formation of an ethylene oxide product containing less than 0.0010% aldehyde-type impurities and is practically completely free from formaldehyde.

EXAMPLE 6

The contaminated ethylene oxide contains, in addition to the ethylene oxide, 1.2 wt.% water and 0.028 wt.% aldehyde-type impurities, which latter consist of 0.026 wt.% acetaldehyde and 0.002 wt.% formaldehyde.

This is charged into column 11 according to Example 1 at a flow rate of 8,102 kg/hour for distillation under a mean absolute pressure of 4.25 bars. A liquid stream consisting of 44.5% water and 54.5% ethylene oxide leaves the bottom of the column at a rate of 220 kg/hour at a temperature of 58° C. The gas stream leaving the column at its top at a temperature of 50° C. at a flow rate of 51,233 kg/hour is formed by ethylene oxide that is practically free from any water as in all the preceding examples and only contains less than 0.0015% aldehyde-type impurities.

After condensation of this gas stream, 7,882 kg/hour of the ethylene oxide produced are collected. The ratio of refluxed ethylene oxide to ethylene oxide produced now equals 5.5:1.

EXAMPLE 7

COMPARATIVE

Example 6 is repeated by operating in column 11 such that the water contained in the contaminated ethylene oxide is still present in the liquid withdrawn at the bottom of the column, but the amount of ethylene oxide in this liquid is such that the weight ratio of the ethylene oxide to the water equals 20.

The ethylene oxide produced contains not only a fairly constant amount of aldehyde-type impurities equaling 0.005 wt.%, but also formaldehyde, which still accounts for half this value, i.e., almost the total amount of the formaldehyde present in the contaminated ethylene oxide.

While the invention has been described in connection with a preferred embodiment, it is not intended to limit the scope of the invention to the particular form set forth, but, on the contrary, it is intended to cover such alternatives, modifications, and equivalents as may be included within the spirit and scope of the invention as defined by the appended claims.

We claim:

1. In the process for separating ethylene oxide from aldehyde impurities in contaminated ethylene oxide containing the said aldehyde impurities, as well as water, by distilling the said contaminated ethylene oxide in a reflux column having a top and a bottom, the improvement comprising introducing the contaminated ethylene oxide into a lower level of the reflux column and distilling by refluxing said contaminated ethylene oxide under conditions such that there is a separation of the aldehyde impurities from the contaminated ethylene oxide and the fluid stream leaving the bottom of said reflux column contains the water present in the contaminated ethylene oxide and ethylene oxide in amounts corresponding, on a weight basis, to 0.15 to 3 times the weight of the water in said bottom fluid stream, and the ethylene oxide resulting from the separation of the aldehyde impurities leaves said column at its top.

2. The process in accordance with claim 1, wherein the weight ratio of ethylene oxide to water in the fluid stream leaving the bottom of the column is between 0.3 and 1.5.

3. The process in accordance with claim 2, wherein the amount of aldehyde impurities in the contaminated ethylene oxide relative to the amount of ethylene oxide is between 0.005 wt.% and 0.02 wt.%.

4. The process in accordance with claim 3, wherein the contaminated ethylene oxide contains an amount of ethylene oxide equaling or exceeding 80 wt.%.

5. The process in accordance with claim 4, wherein the contaminated ethylene oxide contains an amount of water equaling or exceeding 0.5 wt.%.

6. The process in accordance with claim 5, wherein the column operates at a mean absolute pressure between 2.5 and 5 bars.

7. The process in accordance with claim 6, wherein the temperature at the bottom of the column is between 40° C. and 60° C.

8. The process in accordance with claim 7, wherein the column comprises a number of theoretical plates between 30 and 60.

9. The process in accordance with claim 8, wherein the contaminated ethylene oxide enters the column at a level located between half and three-fourths the number of theoretical plates counted from the top of the column.

10. The process in accordance with claim 9, wherein the distillation results in a reflux consisting of a condensed fraction of ethylene oxide separated from the aldehyde impurities and a nonrefluxed ethylene oxide such that the weight ratio of the refluxed ethylene oxide to the nonrefluxed ethylene oxide is between 1 and 9.

11. The process in accordance with claim 10, wherein the weight ratio of the refluxed ethylene oxide to the nonrefluxed ethylene oxide is between 1.5 and 6.

12. A process for isolating ethylene oxide separated from aldehyde impurities in a gas stream leaving the zone of gas-phase catalytic oxidation of ethylene by oxygen, comprising:
(a) contacting the said contaminated ethylene oxide gas stream with an essentially aqueous stream to obtain a dilute contaminated ethylene oxide solution,
(b) subjecting said dilute aqueous contaminated ethylene oxide solution to steam distillation in a column having a top and a bottom operating under a mean absolute pressure between 1.5 and 6 bars to obtain an aqueous stream essentially freed from ethylene oxide at the bottom of the column and, at the top of the column, a fluid stream which contains ethylene oxide contaminated with aldehyde impurities and progressively condensing said gas stream in two or three heat exchangers arranged in series and operating at a mean absolute pressure between 1.5 and 6 bars, the temperature of the cold source for the last heat exchanger being between 5° C. and a maximum temperature that is 5° C. lower than the condensation temperature of pure ethylene oxide under the temperature being considered, and
(c) distilling by refluxing the contaminated ethylene oxide fluid stream leaving the last of said heat exchangers by introducing said contaminated ethylene oxide into a lower level of a reflux column and distilling by refluxing said contaminated ethylene oxide under conditions such that there is a separation of the aldehyde impurities from the contaminated ethylene oxide and the fluid stream leaving the bottom of said reflux column contains the water present in the contaminated ethylene oxide and the ethylene oxide in amounts corresponding, on a weight basis, to 0.15 to 3 times the weight of the water in said bottom fluid stream, and the ethylene oxide resulting from the separation of the aldehyde impurities leaves said column at its top.

13. The process in accordance with claim 12, wherein the contaminated ethylene oxide leaving the last of the heat exchangers contains 95 wt.% ethylene oxide or more and 0.003–0.05 wt.% aldehyde impurities.

* * * * *